(12) United States Patent
Ikeda et al.

(10) Patent No.: US 12,358,926 B2
(45) Date of Patent: Jul. 15, 2025

(54) COMPOUND AND APPLICATION THEREOF

(71) Applicants: DAICEL CORPORATION, Osaka (JP); THE UNIVERSITY OF TOKYO, Tokyo (JP)

(72) Inventors: Daiji Ikeda, Tokyo (JP); Takeshi Yokoo, Tokyo (JP); Yasuyuki Akai, Tokyo (JP); Toshihiro Okamoto, Tokyo (JP); Tadanori Kurosawa, Tokyo (JP); Junichi Takeya, Tokyo (JP); Dinghai Cen, Shanghai (CN)

(73) Assignees: DAICEL CORPORATION, Osaka (JP); THE UNIVERSITY OF TOKYO, Tokyo (JP)

( * ) Notice: Subject to any disclaimer, the term of this patent is extended or adjusted under 35 U.S.C. 154(b) by 431 days.

(21) Appl. No.: 17/800,692

(22) PCT Filed: Feb. 19, 2020

(86) PCT No.: PCT/CN2020/075847
§ 371 (c)(1),
(2) Date: Aug. 18, 2022

(87) PCT Pub. No.: WO2021/163921
PCT Pub. Date: Aug. 26, 2021

(65) Prior Publication Data
US 2023/0128569 A1 Apr. 27, 2023

(51) Int. Cl.
*C07D 495/14* (2006.01)
*H10K 10/46* (2023.01)
*H10K 85/60* (2023.01)

(52) U.S. Cl.
CPC ......... *C07D 495/14* (2013.01); *H10K 10/484* (2023.02); *H10K 85/6576* (2023.02)

(58) Field of Classification Search
None
See application file for complete search history.

(56) References Cited

U.S. PATENT DOCUMENTS

| | | | |
|---|---|---|---|
| 7,834,198 | B2 | 11/2010 | Takimiya et al. |
| 8,084,624 | B2 | 12/2011 | Takimiya et al. |
| 8,110,714 | B2 | 2/2012 | Nagata et al. |
| 8,236,998 | B2 | 8/2012 | Nagata et al. |

(Continued)

FOREIGN PATENT DOCUMENTS

| | | |
|---|---|---|
| EP | 3 125 322 A1 | 2/2017 |
| WO | WO2005/080304 A1 | 9/2005 |
| WO | WO2006/077888 A1 | 7/2006 |
| WO | WO2013/125599 A1 | 8/2013 |

OTHER PUBLICATIONS

Extended European Search Report dated Oct. 11, 2023 for Application No. 20919948.8.
International Preliminary Report on Patentability and Written Opinion of the International Searching Authority for International Application No. PCT/CN2020/075847, dated Sep. 1, 2022, with an English translation.
International Search Report for International Application No. PCT/CN2020/075847, dated Oct. 27, 2020, with English translation.

*Primary Examiner* — Anthony Ho
(74) *Attorney, Agent, or Firm* — Birch, Stewart, Kolasch & Birch, LLP

(57) ABSTRACT

Provided is a compound that is excellent in chemical stability, has high solubility in a solvent, and exhibits excellent carrier mobility.

(Continued)

A compound represented by Formula (1):

[Chem. 1]

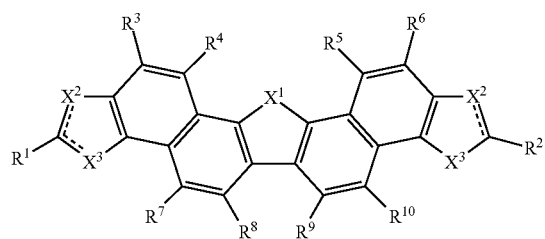

(1)

where in Formula (1), $X^1$, $X^2$, $X^3$, and $R^1$ to $R^{10}$ are as defined in the specification.

18 Claims, 1 Drawing Sheet

(56) References Cited

U.S. PATENT DOCUMENTS

| | | |
|---|---|---|
| 9,537,110 B2 | 1/2017 | Takeya et al. |
| 2008/0061287 A1 | 3/2008 | Nagata et al. |
| 2009/0001357 A1 | 1/2009 | Takimiya et al. |
| 2011/0024731 A1 | 2/2011 | Takimiya et al. |
| 2012/0108850 A1 | 5/2012 | Nagata et al. |
| 2014/0034915 A1 | 2/2014 | Lee et al. |
| 2015/0014673 A1 | 1/2015 | Takeya et al. |

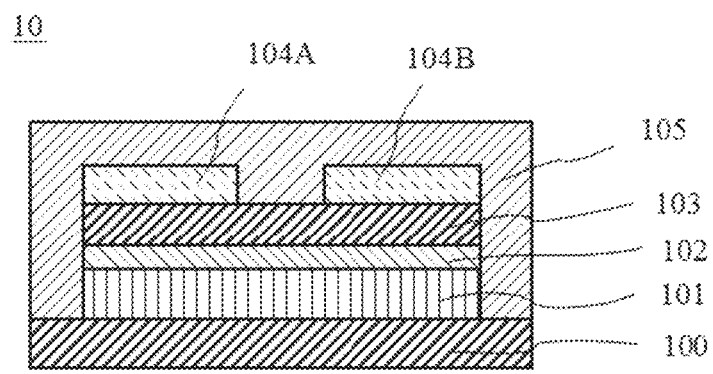

COMPOUND AND APPLICATION THEREOF

TECHNICAL FIELD

The present invention relates to a novel compound and an application thereof. More specifically, the invention relates to a novel compound and a method for manufacturing the same, an organic semiconductor solution composition containing the compound, an organic semiconductor film formed from the organic semiconductor solution composition, and an organic thin film transistor having the organic semiconductor film.

BACKGROUND ART

Organic semiconductor materials are drawing attention, as they can be processed at lower temperatures than inorganic semiconductor materials and are advantageous in that manufacturing costs can be reduced, and a flexible substrate device or the like can be enlarged by a solution process. Various organic semiconductor materials have been actively researched and developed.

Acene compounds, such as pentacene or tetracene, have been known for a while and are organic semiconductor materials having high carrier mobility, but they have issues with chemical stability and low solubility in a solvent.

Patent Document 1 discloses an organic compound with improved chemical stability by replacing a part of an acene skeleton with sulfur, selenium, or the like, and Patent Document 2 discloses an organic compound with having improved solubility by introducing a substituent group into an acene skeleton.

Patent Document 3 discloses that an organic compound having a thiophene structure or a furan structure in its basic skeleton with a substituent such as an alkyl group introduced therein, and containing a non-linear molecular structure with low symmetry, has further improved chemical stability and solubility while exhibiting high carrier mobility.

However, in these organic semiconductor materials, semiconductor properties (carrier mobility and the like) are likely to deteriorate due to intermolecular deviation caused by molecular fluctuation in a crystal structure accompanying a temperature change, a crystal grain boundary present in an organic semiconductor film, a deformed portion due to an external force applied to the organic semiconductor film, and the like, and there is still room for improvement.

CITATION LIST

Patent Document

Patent Document 1: WO 2006/077888
Patent Document 2: WO 2005/080304
Patent Document 3: WO 2013/125599

SUMMARY OF INVENTION

Technical Problem

An object of the present invention is to provide a compound that is excellent in chemical stability, has a high solubility in a solvent, and exhibits excellent carrier mobility.

Another object of the present invention is to provide a method for manufacturing the compound. Also, still another object of the present invention is to provide an organic semiconductor solution composition containing the compound described above.

Still another object of the present invention is to provide an organic semiconductor film formed from the organic semiconductor solution composition described above.

Moreover, still another object of the present invention is to provide an organic thin film transistor having the organic semiconductor film described above.

Solution to Problem

In order to solve the above-described issues, the present inventors have examined on the basis of an idea that, when two π-electron orbitals showing different orbital shapes can be allowed to contribute to the overlap of orbitals by degenerating the highest occupied molecular orbital (HOMO) and the next highest occupied molecular orbital (NHOMO), the carrier mobility is improved, and influence of the intermolecular deviation is also reduced. As a result, the inventors have found that a certain dinaphthochalcogenophene fused ring compound exhibits high carrier mobility. The present invention has been completed based on such findings.

Specifically, the present invention provides a compound represented by Formula (1) below:

[Chem. 1]

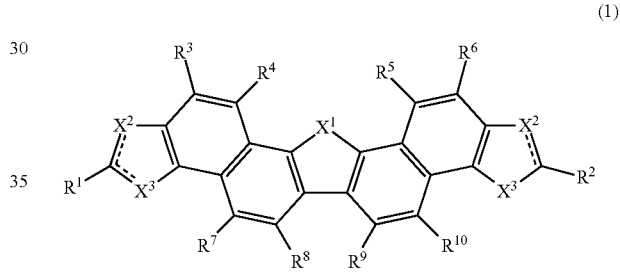

(1)

where in Formula (1), $X^1$ is an oxygen atom, a sulfur atom, a selenium atom, or a tellurium atom; $X^2$ and $X^3$, which may be the same or different, are each a carbon atom, an oxygen atom, a sulfur atom, a selenium atom, or a tellurium atom, with the proviso that a case of $X^2$ and $X^3$ being simultaneously carbon atoms is excluded; $R^1$ and $R^2$, which may be the same or different, are each a hydrogen atom or an organic group, and $R^3$ to $R^{10}$, which may be the same or different, are each a hydrogen atom, a halogen atom, or an organic group; $R^3$ and $R^4$, $R^5$ and $R^6$, $R^7$ and $R^8$, $R^8$ and $R^9$, and $R^9$ and $R^{10}$ may each bond to each other to form a ring together with an adjacent carbon atom; and a double line including a dashed line represents a single bond or a double bond.

Also, the present invention provides a compound represented by Formula (1') below:

[Chem. 2]

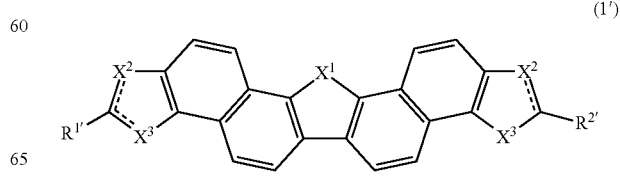

(1')

where in Formula (1') $X^1$, $X^2$ and $X^3$ are the same as those in Formula (1); $R^{1'}$ and $R^{2'}$ are the same or different organic groups; and a double line including a dashed line represents a single bond or a double bond.

In Formula (1'), it is preferable that $X^1$ be a sulfur atom; that one of $X^2$ and $X^3$ be a carbon atom and the other be a sulfur atom; and that $R^{1'}$ and $R^{2'}$ be the same or different organic groups.

The present invention also provides a method of manufacturing the compound described above, including obtaining a compound represented by Formula (1-5) from a compound represented by Formula (1-4):

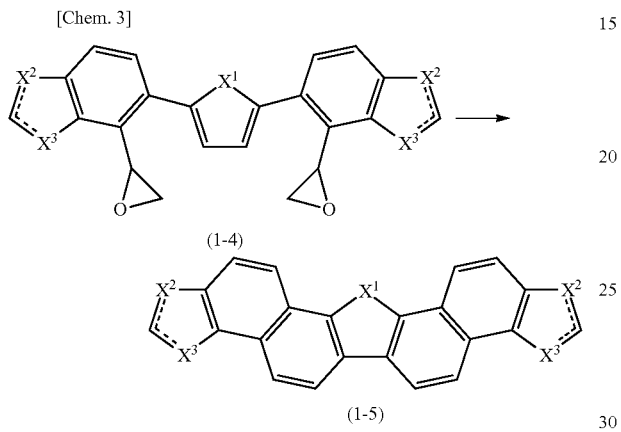

where in Formulas (1-4) and (1-5), $X^1$, $X^2$, $X^3$, and the double line including a dashed line indicate the same contents as those in Formula (1).

The present invention also provides an organic semiconductor solution composition containing the compound described above and at least one solvent.

The present invention also provides an organic semiconductor film formed from the organic semiconductor solution composition described above.

The present invention also provides an organic thin film transistor having the organic semiconductor film described above.

Advantageous Effects of Invention

The compound according to an embodiment of the present invention is excellent in chemical stability and has high solubility in a solvent, and thus it is possible to form an organic semiconductor film with a large area and high uniformity by application, printing, and the like of an organic semiconductor solution composition.

The organic semiconductor film according to an embodiment of the present invention exhibits excellent carrier mobility, and thus a high performance organic thin film transistor can be realized.

BRIEF DESCRIPTION OF DRAWING

The sole drawing figure is a cross-sectional schematic view illustrating a top contact/bottom gate type organic thin film transistor.

DESCRIPTION OF EMBODIMENTS

The compound according to an embodiment of the present invention, the method for manufacturing the compound (organic semiconductor material), the organic semiconductor solution composition containing the compound, the organic semiconductor film formed from the organic semiconductor solution composition, and the organic thin film transistor having the organic semiconductor film will be described below.

[Compound]

The compound according to an embodiment of the present invention is represented by Formula (1):

[Chem. 4]

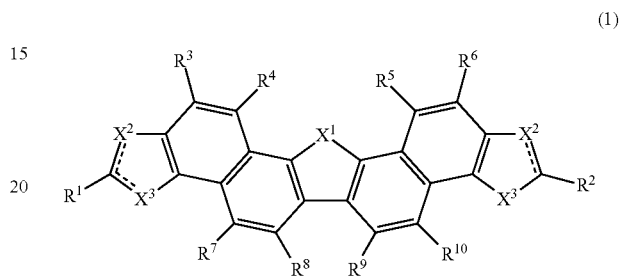

(1)

In Formula (1), $X^1$ is an oxygen atom, a sulfur atom, a selenium atom, or a tellurium atom; and $X^2$ and $X^3$, which may be the same or different, are each a carbon atom, an oxygen atom, a sulfur atom, a selenium atom, or a tellurium atom, with the proviso that a case of $X^2$ and $X^3$ being simultaneously carbon atoms is excluded. $R^1$ and $R^2$, which may be the same or different, are each a hydrogen atom or an organic group, and $R^3$ to $R^{10}$, which may be the same or different, are each a hydrogen atom, a halogen atom, or an organic group. $R^3$ and $R^4$, $R^5$ and $R^6$, $R^7$ and $R^8$, $R^8$ and $R^9$, and $R^9$ and $R^{10}$ may each bond to each other to form a ring together with an adjacent carbon atom.

The $X^1$ in Formula (1) is preferably a sulfur atom or a selenium atom from the perspective of exhibiting a higher carrier mobility and is more preferably a sulfur atom from the perspective of further improving chemical stability.

In Formula (1), it is preferable that one of $X^2$ and $X^3$ be a sulfur atom or a selenium atom and that the other be a carbon atom, and it is more preferable that the $X^2$ be a sulfur atom and that the $X^3$ be a carbon atom, from the perspective of exhibiting a higher carrier mobility.

The organic groups according to $R^1$ and $R^2$ in Formula (1) are preferably alkyl groups having from 1 to 40 carbon atoms, alkenyl groups having from 2 to 22 carbon atoms, alkynyl groups having from 2 to 22 carbon atoms, aryl groups having from 6 to 20 carbon atoms, cycloalkyl groups having from 3 to 40 carbon atoms, alkoxy groups having from 1 to 20 carbon atoms, or monovalent heterocyclic groups, and more preferably aryl groups having from 1 to 40 carbon atoms, aryl groups having from 6 to 20 carbon atoms, or monovalent heterocyclic groups. These groups may have a substituent.

The alkyl groups according to $R^1$ and $R^2$ described above are linear or branched alkyl groups having preferably from 1 to 20 carbon atoms, more preferably from 3 to 20 carbon atoms, and even more preferably from 5 to 15 carbon atoms, and examples thereof include methyl groups, ethyl groups, propyl groups, 2-methylpropyl groups, butyl groups, pentyl groups, 1-methylpentyl groups, 2,2-dimethylpropyl groups, hexyl groups, 1-methylpentyl groups, heptyl groups, octyl groups, nonyl groups, decyl groups, undecyl groups, dodecyl groups, tridecyl groups, tetradecyl groups, pentadecyl groups, 2,6-dimethyloctyl groups, icosyl groups, 2-decyltetradecyl groups, 2-hexyldodecyl groups, 2-ethyloctyl groups, 2-decyltetradecyl groups, 2-butyldecyl groups, 1-octylnonyl groups, 2-ethyloctyl groups, 2-octyldecyl groups, 2-octyldodecyl groups, 7-hexylpentadecyl groups, 2-octyltetradecyl groups, and 2-ethylhexyl groups.

The alkenyl groups according to $R^1$ and $R^2$ described above are linear or branched alkenyl groups having preferably from 2 to 18 carbon atoms, more preferably from 2 to 12 carbon atoms, and even more preferably from 2 to 8 carbon atoms, and examples thereof include vinyl groups, 1-propenyl groups, 2-propenyl groups, 2-methyl-1-propenyl groups, 1-butenyl groups, 2-butenyl groups, 3-butenyl groups, 3-methyl-2-butenyl groups, 1-pentenyl groups, 2-pentenyl groups, 3-pentenyl groups, 4-pentenyl groups, 4-methyl-3-pentenyl groups, 1-hexenyl groups, 3-hexenyl groups, 5-hexenyl groups, 1-heptenyl groups, 1-octenyl groups, 1-nonenyl groups, and 1-decenyl.

The alkynyl groups according to $R^1$ and $R^2$ described above are linear or branched alkynyl groups having preferably from 2 to 18 carbon atoms, more preferably from 2 to 12 carbon atoms, and even more preferably from 2 to 8 carbon atoms, and examples thereof include ethynyl groups, 1-propynyl groups, 2-propynyl groups, 1-butynyl groups, 2-butynyl groups, 3-butynyl groups, 1-pentynyl groups, 2-pentynyl groups, 3-pentynyl groups, 4-pentynyl groups, 1-hexynyl groups, 2-hexynyl groups, 3-hexynyl groups, 4-hexynyl groups, 5-hexynyl groups, 1-heptynyl groups, 1-octynyl groups, 1-nonynyl groups, 1-decynyl groups, trimethylsilylethynyl groups, triethylsilylethynyl groups, tri-i-propylsilylethynyl groups, and 2-p-propylphenylethynyl groups.

The aryl groups according to the $R^1$ and $R^2$ described above are aryl groups having preferably from 6 to 18 carbon atoms, and more preferably from 6 to 14 carbon atoms, and examples thereof include phenyl groups, naphthyl groups, anthryl groups, phenanthryl groups, acenaphthylenyl groups, biphenylyl groups, 2,4,6-trimethylphenyl groups, p-(t-butyl) phenyl groups, 4-methyl-2,6-dipropylphenyl groups, 4-fluorophenyl groups, 4-trifluoromethylphenyl groups, p-pentylphenyl groups, 3,4-dipentylphenyl groups, p-heptoxyphenyl groups, and 3,4-diheptoxyphenyl groups.

The cycloalkyl groups according to $R^1$ and $R^2$ described above are cyclic alkyl groups having preferably from 3 to 20 carbon atoms, and more preferably from 4 to 20 carbon atoms, and examples thereof include cyclopropyl groups, cyclobutyl groups, cyclopentyl groups, a cyclohexyl groups, cycloheptyl groups, cyclooctyl groups, cyclononyl groups, cyclodecyl groups, and adamantyl groups.

The alkoxy groups according to $R^1$ and $R^2$ described above are linear or branched alkoxy groups having preferably from 1 to 18 carbon atoms, more preferably from 1 to 12 carbon atoms, and even more preferably from 1 to 8 carbon atoms, and examples thereof include methoxy groups, ethoxy groups, n-propoxy groups, isopropoxy groups, n-butoxy groups, isobutoxy groups, sec-butoxy groups, tert-butoxy groups, n-pentyloxy groups, isopentyloxy groups, neopentyloxy groups, tert-pentyloxy groups, n-hexyloxy groups, isohexyloxy groups, heptyloxy groups, octyloxy groups, nonyloxy groups, and decyloxy groups.

Examples of the monovalent heterocyclic groups according to $R^1$ and $R^2$ described above include from 5- to 22-membered (preferably 5- or 6-membered) aromatic heterocyclic groups and aliphatic heterocyclic groups having in the ring at least one carbon atom and from 1 to 4 heteroatoms selected from an oxygen atom, a sulfur atom and a nitrogen atom.

Examples of the aromatic heterocyclic group include monocyclic aromatic heterocyclic groups (such as a furanyl group, a 2-hexylfuranyl group, a thienyl group, a pyridyl group, a pyrimidinyl group, a pyrrolyl group, an imidazolyl group, a pyrazolyl group, a thiazolyl group, a benzthiazolyl group, a benzoxazolyl group, a benzimidazolyl group, and a selenophenyl group), and fused aromatic heterocyclic groups (such as a quinolyl group and an isoquinolyl group).

Examples of the aliphatic heterocyclic group include monocyclic non-aromatic heterocyclic groups (such as a piperidyl group, a morpholinyl group, a piperazinyl group, and a tetrahydrofuryl group) and fused non-aromatic heterocyclic groups (such as a chromenyl group, a tetrahydroquinolinyl group, and a tetrahydroisoquinolinyl group).

Examples of the substituent that $R^1$ and $R^2$ may have include halogen atoms (such as a fluorine atom), cyano groups, hydroxyl groups, nitro groups, acyl groups (such as a hexanoyl group and a benzoyl group), alkoxy groups (such as a butoxy group), aryloxy groups (such as a phenoxy group), silyloxy groups, heterocyclic oxy groups, acyloxy groups, carbamoyloxy groups, amino groups, anilino groups, acylamino groups, aminocarbonylamino groups (such as an ureido group), alkoxy and aryloxycarbonylamino groups, alkyl and arylsulfonylamino groups, mercapto groups, alkyl and arylthio groups (such as a methylthio group and an octylthio group), heterocyclic thio groups, sulfamoyl groups, sulfo groups, alkyl and arylsulfinyl groups, alkyl and arylsulfonyl groups, alkyl and aryloxycarbonyl groups, carbamoyl groups, aryl and heterocyclic azo groups, imide groups, phosphino groups, phosphinyl groups, phosphinyloxy groups, phosphinylamino groups, phosphono groups, silyl groups (such as a ditrimethylsiloxymethylbutoxy group), hydrazino groups, ureido groups, boronic acid groups (—B(OH)$_2$), phosphato groups (—OPO(OH)$_2$), sulphato groups (—OSO$_3$H), and other known substituents.

Examples of the halogen atom in Formula (1) above include a fluorine atom, a chlorine atom, a bromine atom, and an iodine atom, and, among others, a fluorine atom is preferred because it exhibits a higher carrier mobility.

The organic groups according to the above $R^3$ to $R^{10}$ in Formula (1) are the same as those according to the above $R^1$ and $R^2$. Among others, alkyl groups having from 1 to 40 carbon atoms, aryl groups having from 6 to 20 carbon atoms, or alkoxy groups having from 1 to 20 carbon atoms are preferred.

Also, substituents which these groups may have are the same as those according to the above $R^1$ and $R^2$.

$R^3$ and $R^4$, $R^5$ and $R^6$, $R^7$ and $R^8$, $R^8$ and $R^9$, and $R^9$ and $R^{10}$, which are combinations of adjacent groups, in the above $R^3$ to $R^{10}$, may bond to each other to further form a ring. The ring described above may be an aromatic ring, or may be a non-aromatic ring.

In Formula (1), for $X^2$, $X^3$, and a five-membered ring with the double lines including a dash line, those are non-aromatic rings if both of the double lines including a dashed line are single bonds and are aromatic rings if one of them is a double bond.

The compound according to an embodiment of the present invention has high solubility in a solvent due to the introduction of a flexible dinaphthochalcogenophene type structure and substituents, and thus can be used to prepare an organic semiconductor solution composition described below at a desired concentration. Therefore, it can be suitably used to manufacture an organic semiconductor film by simple solution processes such as application methods and printing methods.

Since the compound according to an embodiment of the present invention has excellent chemical stability, it can also be used in the manufacture of an organic semiconductor film by gas phase processes such as vacuum vapor deposition, molecular beam epitaxy (MBE), sputtering, laser deposition, and gas phase transport growth.

Also, the compound according to an embodiment of the present invention stably exhibits excellent carrier mobility. The reason for this has not been completely elucidated yet, but it is assumed that the energy levels of HOMO and NHOMO are very close due to the structure having five-membered heterocyclic rings at both ends, and that NHOMO as well as HOMO contributes to overlap of R-electron orbitals.

Among the compounds according to an embodiment of the present invention, the compound represented by Formula (1') is preferred from the perspective of achieving both compatibility with a solvent and overlap of orbitals at an appropriate level.

[Chem. 5]

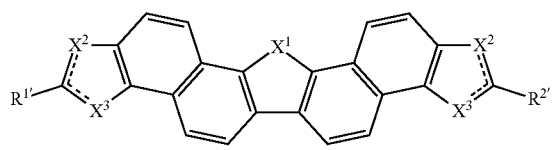

(1')

where in Formula (1'), $X^1$, $X^2$ and $X^3$ are the same as those in Formula (1); $R^{1'}$ and $R^{2'}$ are the same or different organic groups; and a double line including a dashed line represents a single bond or a double bond.

The organic groups according to $R^1$ and $R^2$ in Formula (1') are preferably alkyl groups having from 1 to 40 carbon atoms, alkenyl groups having from 2 to 22 carbon atoms, alkynyl groups having from 2 to 22 carbon atoms, aryl groups having from 6 to 20 carbon atoms, cycloalkyl groups having from 3 to 20 carbon atoms, alkoxy groups having from 1 to 20 carbon atoms, or monovalent heterocyclic groups.

The alkyl groups, alkenyl groups, alkynyl groups, aryl groups, monovalent heterocyclic groups, cycloalkyl groups, alkoxy groups, and substituent which these groups may have, are the same as those according to $R^1$ and $R^2$ in Formula (1') above.

The contents of the $X^1$, $X^2$, $X^3$, and double line including a dashed line in Formula (1') above are the same as in Formula (1) above.

Among the compounds represented by Formula (1') above, a compound in which $X^1$ is a sulfur atom, one of $X^2$ and $X^3$ is a carbon atom and the other is a sulfur atom, and $R^{1'}$ and $R^{2'}$ are the same or different organic groups is more preferred.

Among the compounds represented by Formula (1') above, a compound in which $X^1$ is a sulfur atom, $X^2$ is a sulfur atom, and $X^3$ is a carbon atom, and $R^{1'}$ and $R^{2'}$ are the same or different organic groups, which is the compound represented by Formula (1''), is even more preferred.

[Chem. 6]

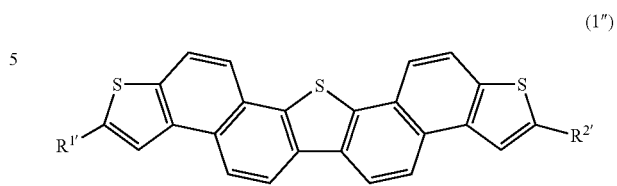

(1'')

The organic groups according to $R^{1'}$ and $R^{2'}$ in Formula (1'') above are alkyl groups having from 1 to 40 carbon atoms, aryl groups having from 6 to 20 carbon atoms, or monovalent heterocyclic alkyl groups, aryl groups, or monovalent heterocyclic groups, and are the same as those in Formula (1') above.

Method for Manufacturing Compound

The compound represented by Formula (1) according to an embodiment of the present invention can be manufactured, for example, by cross-coupling a compound represented by Formula (1-1) below and a compound represented by Formula (1-2) below to obtain a compound represented by Formula (1-3) below, and then epoxidizing a formyl group of the compound represented by the formula (1-3) to obtain a compound represented by Formula (1-4) below; obtaining a compound represented by Formula (1-5) below from the compound represented by the formula (1-4) through fused ring formation; and further introducing a substituent into the compound represented by the formula (1-5).

Cross-Coupling, and Epoxidation of Formyl Group

The compound represented by Formula (1-4) can be manufactured by cross-coupling a compound represented by Formula (1-1) and a compound represented by Formula (1-2) to obtain a compound represented by Formula (1-3) and then converting a formyl group of the compound represented by Formula (1-3) into an epoxy group.

[Chem. 7]

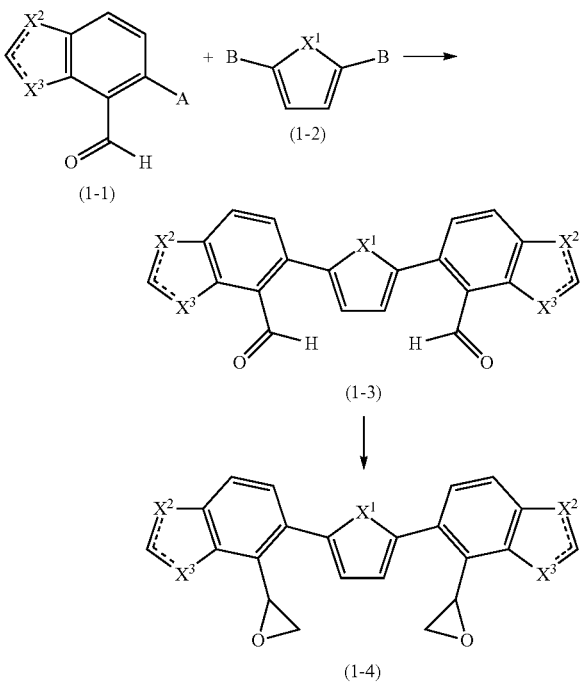

In Formulas (1-1) to (1 to 4), $X^1$, $X^2$, $X^3$, and the double line including a dashed line indicate the same contents as those in Formula (1), A represents an organic sulfonyloxy group, and B represents a boronic acid group (—B(OH)$_2$).

Examples of the organic sulfonyl oxy group include methanesulfonylyloxy groups, p-toluenesulfonyloxy groups, trifluoromethylsulfonylyloxy groups, and camphorsulfonyloxy groups. Among others, trifluoromethylsulfonylyloxy groups are preferred.

The above B may be a boronic acid ester group (boronic acid pinacol ester group, boronic acid diisopropyl ester group, boronic acid propylene glycol ester group, or the like).

In the obtainment of the compound represented by Formula (1-3), the compound represented by Formula (1-1) and the compound represented by Formula (1-2) are cross-coupled under general Suzuki-Miyaura coupling conditions.

The compound represented by Formula (1-1) can be synthesized using a known techniques such as methoxy substituent of the halogen atom, formylation of the group at position 4, deprotection of the methoxy group, or organic sulfonyloxylation, using 5-halogenated benzofuran, 5-halogenated benzothiophene, or the like as a starting raw material.

The compound represented by Formula (1-2) can be synthesized by a known technique of reacting furan, thiophene, or the like with diborane, introducing a boronic acid group (—B(OH)$_2$), and, if necessary, esterifying the boronic acid group. Also, the compound can also be a commercially available product.

The compound represented by Formula (1-4) can be obtained by a reaction of epoxidizing the formyl group of the compound represented by Formula (1-3) in the presence of a sulfur ylide obtained by reacting a metal hydroxide with a sulfonium compound or a sulfoxonium compound in the system.

Examples of the sulfonium compound can include trimethylbromosulfur (Me$_3$SBr), trimethylchlorosulfur (Me$_3$SCl), and trimethyliodosulfur (Me$_3$SI), and examples of the sulfoxonium compound can include trimethyloxobromosulfur (Me$_3$OSBr), trimethyloxochlorosulfur (Me$_3$OSCl), and trimethyloxoiodosulfur (Me$_3$OSI). These may be used alone, or two or more thereof may be used in combination.

The reaction temperature (solution temperature) of the reaction to convert the formyl group into an epoxy group is preferably from 0 to 100° C., and more preferably from 50 to 80° C. The reaction time is usually from 1 to 50 hours, and preferably from 1 to 25 hours.

Examples of a base catalyst include KOH and NaOH. These may be used alone, or two or more thereof may be used in combination.

An amount of the base catalyst to be used is preferably from 1 to 10 mol, based on 1 mol of the compound represented by Formula (1-3).

The use amount of Me$_3$SI is preferably from 2 to 4 mol, based on 1 mol of the compound represented by Formula (1-3).

Formation of Fused Ring

In the step of obtaining the compound represented by Formula (1-5), a fused ring containing an aromatic six-membered ring with carbon constituting the epoxy group in the compound represented by Formula (1-4) is formed in the presence of a Lewis acid catalyst.

[Chem. 8]

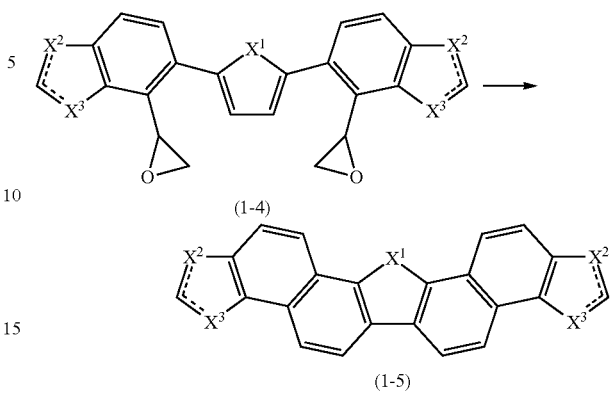

In Formulas (1-4) and (1-5), $X^1$, $X^2$, $X^3$, and the double line including a dashed line indicate the same contents as those in Formula (1).

The reaction temperature (solution temperature) is preferably from 0 to 120° C., and more preferably from 20 to 100° C. The reaction time is usually from 1 to 100 hours, and preferably from 1 to 50 hours.

Examples of the Lewis acid catalyst include indium (III) chloride, aluminum chloride (III), and thallium chloride (III). These may be used alone, or two or more thereof may be used in combination.

The amount of the Lewis catalyst to be used is preferably from 0.1 to 2 mol, based on 1 mol of the compound represented by Formula (1-1).

Introduction of Substituent

The compound represented by Formula (1) above can be obtained by introducing the halogen atoms or organic groups in $R^1$ to $R^{10}$ of the above formula into the compound represented by Formula (1-5) using a known aromatic substitution reaction or a known cross-coupling reaction.

The compound represented by Formula (1') according to an embodiment of the present invention can likewise be obtained by introducing, into the compound represented by Formula (1-5) above, the organic groups according to the above $R^{1'}$ and $R^{2'}$.

The compound represented by Formula (1") according to an embodiment of the present invention can likewise be obtained, for example, by introducing the organic groups in $R^{1'}$ and $R^{2'}$ into the compound represented by Formula (1-5) above obtained using, for example, 4-formyl-5-trifluoromethylsulfonyloxybenzothiophene as the compound represented by Formula (1-1) above and 2,5-thiopheniboronic acid as the compound represented by Formula (1-2) above.

The reactions to obtain the compounds represented by Formulas (1), (1'), and (1") above and Formulas (1-1) to (1-5) above are preferably performed in the presence of a solvent.

Examples of the solvent include water, alcohol solvents (methanol, ethanol, isopropanol, butyl cellosolve, etc.), nitrogen-containing solvents (acetonitrile, N-methyl-2-pyrrolidone, N,N-dimethylformamide, and the like), halogenated hydrocarbon solvents (dichloromethane, chloroform, 1,2-dichloroethane, chlorobenzene, dichlorobenzene, etc.), ether solvents (diethyl ether, t-butyl methyl ether, tetrahydrofuran, 1,4-dioxane, dimethoxyethane, dichloromethylmethyl ether, etc.), glycol solvents (ethylene glycol, propylene glycol monomethyl ether-2-acetate, etc.), aromatic hydrocarbon solvents (benzene, toluene, xylene, anisole, etc.), ketone solvents (methyl isobutyl ketone, acetone, etc.), ester solvents (ethyl acetate, ethyl lactate, γ-butyrolactone, etc.) These may be used alone, or two or more thereof may be used in combination.

Furthermore, the compounds represented by Formulas (1-1) to (1-5) obtained in the respective reactions may be purified by a known purification method such as column chromatography or recrystallization and then used in the following reactions, or may be used as crude products in the following reactions.

Organic Semiconductor Solution Composition

The organic semiconductor solution composition according to an embodiment of the present invention contains the above compound (organic semiconductor material) and a solvent. The organic semiconductor materials may be used alone, or two or more thereof may be used in combination.

Solvent

Examples of the solvent include organic solvents such as aliphatic hydrocarbon solvents (pentane, hexane, heptane, etc.), halogenated hydrocarbon solvents (dichloromethane, chloroform, 1,2-dichloroethane, etc.), ether solvents (diethyl ether, t-butyl methyl ether, tetrahydrofuran, dioxane, etc.), alcohol solvents (methanol, ethanol, isopropanol, butyl cellosolve, etc.), ester solvents (ethyl acetate, ethyl lactate, γ-butyrolactone, etc.), ketone solvents (methyl isobutyl ketone, acetone, etc.), nitrogen-containing solvents (acetonitrile, N-methyl-2-pyrrolidone, N,N-dimethylformamide, or the like), sulfur-containing solvents (e.g., dimethyl sulfoxide), halogenated aromatic hydrocarbon solvents (chlorobenzene, 1,2-dichlorobenzene, 1,3-dichlorobenzene, 1,4-dichlorobenzene, 1-chloronaphthalene, 2-chloronaphthalene, 4-chlorobiphenyl, etc.), aromatic hydrocarbon solvents (benzene, toluene, xylene, etc.), and alicyclic hydrocarbon solvents (cyclohexane, cyclopentanone, cyclohexanone, etc.).

A boiling point of the solvent is preferably from 20 to 120° C., and more preferably from 20 to 100° C.

A water content of the solvent used in the composition according to an embodiment of the present disclosure is preferably 0.25 wt. % or less. When the water content in the composition according to an embodiment of the present disclosure is high, the carrier mobility tends to decrease due to inhibition of crystallization or trapping of moisture by the carrier. The water content is preferably 0.15 wt. % or less, more preferably 0.05 wt. % or less. Note that the water content can be measured by the Karl Fischer method.

In addition to the organic semiconductor material and the solvent, the organic semiconductor solution composition according to an embodiment of the present invention may contain a macromolecular compound as a binder, if necessary.

When the organic semiconductor solution composition contains a macromolecular compound, film formability of the organic semiconductor solution composition is improved. For example, film formation can be performed using the edge casting method or the continuous edge casting method described below, even when an organic semiconductor material having a low solubility is used.

Macromolecular Compound

The macromolecular compound that may be contained in the organic semiconductor according to an embodiment of the present invention preferably does not affect electrical properties of the organic semiconductor material, and examples thereof include an epoxy resin, a melamine resin, a phenol resin, a polyurethane resin, acrylic resins (polymethyl methacrylate, poly(2,2,2-trifluoroethyl methacrylate), etc.), polystyrene resins (polystyrene, poly α-methylstyrene, polyvinylphenol, polypentafluorostyrene, etc.), a cellulose resin, butyral resins (e.g., polyvinylbutyral), polyvinyl resins (polyvinyl alcohol, polyvinylacetate, poly(2-vinylpyridine), polyvinyl chloride, polyvinylidene chloride, polytetrafluoroethylene, etc.), a benzocyclobutene resin, silicone resins (e.g., cage-shaped oligosilsesquioxane), polyolefin resins (polyethylene, polypropylene, polycycloolefin, etc.), a polyamide resin, a polyester resin, and a polycarbonate resin.

When the organic semiconductor solution composition according to an embodiment of the present invention contains the macromolecular compound described above, a content of the macromolecular compound is preferably from 0.01 to 20 wt. %, and more preferably from 0.1 to 10 wt. %, per 100 wt. % of the organic semiconductor solution composition. When the content of the macromolecular compound is within this range, the film formability of the organic semiconductor solution composition according to an embodiment of the present disclosure tends to be improved.

A content of the solvent (in the case where two or more solvents are contained, a total amount thereof) in a total amount of the organic semiconductor solution composition according to an embodiment of the present invention is, for example, preferably 99.999 wt. % or less, more preferably 99.990 wt. % or less, and even more preferably 99.900 wt. % or less. A lower limit is, for example, preferably 90 wt. % or greater, more preferably 93 wt. % or greater, and even more preferably 95 wt. % or greater.

A content of a solute (in particular, organic semiconductor material) (in the case where two or more solutes are contained, a total amount thereof) in the organic semiconductor solution composition according to an embodiment of the present invention is, for example, 0.02 parts by weight or greater, preferably 0.03 parts by weight or greater, and particularly preferably 0.04 parts by weight or greater, per 100 parts by weight of the solvent. An upper limit is preferably 1 parts by weight or less, more preferably 0.5 parts by weight or less, and even more preferably 0.1 parts by weight or less.

The organic semiconductor solution composition according to an embodiment of the present invention can be prepared, for example, by mixing the solvent, the solute, and the macromolecular compound to be blended as necessary, and heating the mixture at a temperature of from 30 to 200° C. in an air atmosphere, nitrogen atmosphere, or argon atmosphere for from 0.1 to 5 hours.

The organic semiconductor solution composition according to an embodiment of the present invention can be prepared at various concentrations for the organic semiconductor material having an excellent solubility in the solvent, and a crystallization state of an organic semiconductor film formed therefrom can be broadly and arbitrarily changed from crystalline to amorphous. When the crystallization state of the organic semiconductor film changes, the carrier mobility also changes. Therefore, by using the organic semiconductor solution composition according to an embodiment of the present invention, the crystallization state of the organic semiconductor film can be arbitrarily adjusted, and thus the carrier mobility of the organic semiconductor film can be stably reproduced.

Organic Semiconductor Film

The organic semiconductor film according to an embodiment of the present invention can be formed by applying or printing the above-described organic semiconductor solution composition according to an embodiment of the present invention to a substrate.

Examples of the method of applying or printing the organic semiconductor solution composition onto the substrate include application methods (a drop-casting method, a spin-coating method, a dip-coating method, a blade method, an edge casting method, a continuous edge-casting method, and the like), and printing methods (a screen printing method, an ink-jet printing method, a mask-printing method, an offset printing method, a flexographic printing method, a micro-contact printing method, a lithographic printing method, an intaglio printing method, a letterpress printing method, and the like). Among others, an edge casting method, a continuous edge casting method, or the like is preferable in that an organic monocrystalline semiconductor film having a large surface area is easily obtained at low cost.

Examples of a material for the substrate capable of applying or printing the organic semiconductor solution composition include glass, metals (gold, copper, silver, and the like), inorganic materials (a crystalline silicon substrate, an amorphous silicon substrate, and the like), and resins (a triacetyl cellulose resin, a norbornene resin, a polyester resin, a polyvinyl resin, a polyolefin resin, and the like).

Of these, a resin substrate is preferable in that an organic semiconductor film having a large area can be obtained at low cost.

Drying can be performed, for example, by heating at from 20 to 200° C. for from 0.5 to 24 hours under atmospheric pressure or reduced pressure. Heating may be performed on the organic semiconductor solution composition or may be performed on the substrate.

The organic semiconductor film according to an embodiment of the present invention may also be heat treated after formation for the purpose of controlling the crystal structure and volatilizing the solvent.

A thickness of the organic semiconductor film is preferably from 1 nm to 1000 nm, more preferably from 1 nm to 100 nm, and even more preferably from 1 nm to 50 nm.

The organic semiconductor film according to an embodiment of the present invention may be released from the substrate after formation or may be used in a state of being formed on the substrate or the like.

The organic semiconductor film according to an embodiment of the present invention may be applied uniformly by the application method and then patterned into a predetermined shape by photolithography or the like or may be printed so as to have a predetermined pattern by the printing method.

Organic Thin Film Transistor

The organic thin film transistor according to an embodiment of the present invention includes the organic semiconductor film according to an embodiment of the present invention as a semiconductor layer.

The organic thin film transistor according to an embodiment of the present invention includes, on the substrate, a gate electrode, an organic semiconductor film (semiconductor layer), a gate insulating film provided between the gate electrode and the organic semiconductor film (semiconductor layer), and a source electrode and a drain electrode that are provided in contact with the organic semiconductor film (semiconductor layer) and coupled via the organic semiconductor film (semiconductor layer). In the organic thin film transistor, the organic semiconductor film and the gate insulating film are provided adjacent to each other.

The organic thin film transistor according to an embodiment of the present invention is not particularly limited as long as the organic thin film transistor includes the layers described above. For example, it may have any structure such as a bottom contact type (a bottom contact/bottom gate type, a bottom contact/top gate type), or a top contact type (top contact/bottom gate type, top contact/top gate type), and preferably has a top contact/bottom gate type structure.

A cross-sectional schematic view of a top contact/bottom gate type, which is a preferred example, is shown in the drawing Figure.

Atop contact/bottom gate type organic thin film transistor 10 includes a substrate 100, a conductive film (gate electrode) 101, a gate insulating film 102, an organic semiconductor film 103, a source electrode 104A, a drain electrode 104B, and a protective layer 105.

Examples of applications of the organic thin film transistor according to an embodiment of the present invention include electronic paper, display devices, sensors, electronic tags, and sensors.

EXAMPLES

Hereinafter, the present invention will be described more specifically with reference to examples, but the present invention is not limited by these examples.

The compounds according to the Examples and Comparative Examples were synthesized and the carrier mobility was evaluated.

Method for Evaluating Carrier Mobility

An organic thin film transistor was manufactured by the method, described below, and the carrier mobility under atmospheric pressure of 1 atm (temperature: room temperature) was evaluated using a semiconductor parameter analyzer (4156 C available from Agilent) connected to a semi-auto prober (AX-2000 available from Vector Semiconductor).

The carrier mobility μ (cm$^2$/Vs) was calculated by applying a voltage of −150 V between the source electrode and the drain electrode of the organic thin film transistor and changing the gate voltage in a range of −5 V to −150 V to derive $I_d$, and using the following formula regarding the drain current $I_d$:

$$I_d = (w/2L)\mu C_i (V_g - V_{th})^2$$

In the above equation, L is the gate length, W is the gate width, μ is the carrier mobility, $C_i$ is the capacitance per unit area of the gate insulating film, $V_g$ is the gate voltage, and $V_{th}$ is the threshold voltage.

Identification of Compound

The compounds according to the examples and each intermediate compound were identified by $^1$H-NMR (400 MHz) with tetramethylsilane as an internal standard. A deuterated chloroform (CDCl$_3$) or 1,1,2,2-tetrachloroethane-d2 (CDCl$_2$CDCl$_2$) was used as the solvent.

Example 1

The following compound C10-TBNT was synthesized and the carrier mobility was evaluated.

Synthesis Method

Compound C10-TBNT was synthesized through the following steps.

Synthesis of Intermediate Compound 1b

[Chem. 9]

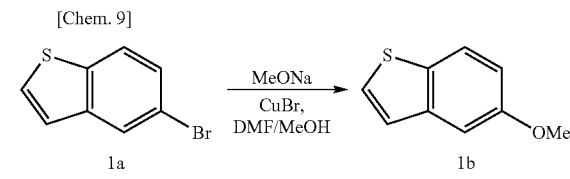 [SMILES: "MeONa" ; Brc1ccc2sccc2c1 ; COc1ccc2sccc2c1]

In the above scheme, MeONa represents sodium methoxide, and DMF represents N,N-dimethylformamide.

Sodium methoxide (19.0 g, 352 mmol) was added to a solution of 5-bromobenzothiophene (50.0 g, 235 mmol) in a mixed solvent of N,N-dimethylformamide and methanol (300 mL, DMF/MeOH=250 mL/50 mL) at room temperature (28° C.) under an argon atmosphere, and the temperature was raised to 110° C. with stirring. Copper bromide (3.37 g, 23.5 mmol) was further added at 110° C., and the suspension was stirred at 110° C. for 5 hours. After cooling the suspension to room temperature, the reaction was ceased by pouring 100 mL of an aqueous ammonium chloride solution into the suspension. It was then extracted with ethyl acetate, dried over sodium sulfate, and concentrated under reduced pressure to obtain a red oil. This was purified by column chromatography (developing solvent=petroleum ether:ethyl acetate=10:1 (volume ratio)) to give compound 1b (34.0 g, 207 mmol, yield: 38%) as a white solid.

$^1$H-NMR (CDCl$_3$, RT) δ: 7.74 (d, 1H, J=8.4 Hz), 7.44 (d, 1H, J=5.6 Hz), 7.28 (d, 1H, J=2.4 Hz), 7.26 (d, 1H, J=5.6 Hz), 7.02 (dd, 1H, J$_1$=2.4 Hz, J$_2$=8.4 Hz), 3.88 (s, 3H)

Synthesis of Intermediate Compound 1c

[Chem. 10]

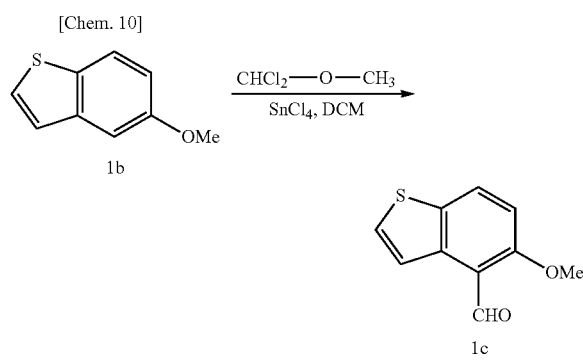

In the above scheme, DCM represents dichloromethane.

Under an argon atmosphere, tin tetrachloride (1 mol/L dichloromethane solution, 124 mL, 124 mmol) was added to a dichloromethane (600 mL) solution of compound 1b (10.0 g, 60.9 mmol) at −40° C., dichloromethyl methyl ether (8.3 mL, 91.3 mmol) was further added thereto, and the mixed liquid was stirred at from −70 to −50° C. for 3 hours. Thereafter, the mixed liquid was left to stand with stirring until the temperature reached room temperature. The mixed liquid was cooled to 0° C., then 500 mL of an aqueous calcium carbonate solution was poured, and the resultant mixed liquid was stirred for 2 hours until no gas was generated. This was extracted with dichloromethane and concentrated under reduced pressure to give a red solid. This was purified by column chromatography (developing solvent=petroleum ether:ethyl acetate=50:1 (volume ratio)) to give compound 1c (9.8 g, 51.2 mmol, yield: 84%) as a red solid.

$^1$H-NMR (CDCl$_3$, RT) δ: 10.74 (s, 1H), 8.42 (d, 1H, J=4.8 Hz), 8.03 (d, 1H, J=9.2 Hz), 7.68 (d, 1H, J=5.2 Hz), 7.09 (d, 1H, J=8.8 Hz), 4.00 (s, 3H)

Synthesis of Intermediate Compound 1d

[Chem. 11]

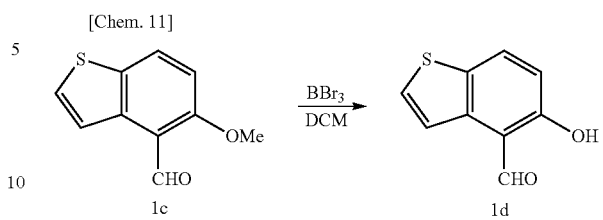

In the above scheme, BBr$_3$ represents boron tribromide.

Boron tribromide (12 mL, 122 mmol) was added to a dichloromethane (1000 mL) solution of compound 1c (19.5 g, 101 mmol) at room temperature (28° C.) under an argon atmosphere, and the mixed liquid was stirred at room temperature (28° C.) for 12 hours. The mixed liquid was cooled to 0° C., then 500 mL of water was poured, and the resultant mixed liquid was stirred for 2 hours. This was extracted with dichloromethane and ethyl acetate and concentrated under reduced pressure to give a red solid. This was purified by column chromatography (developing solvent=dichloromethane) to give compound 1d (16.9 g, 94.9 mmol, yield: 84%) as a red solid.

$^1$H-NMR (CDCl$_3$, RT) δ: 10.55 (s, 1H), 7.07 (d, 1H, J=9.2 Hz), 7.71-7.78 (m, 2H), 7.02 (d, 1H, J=8.8 Hz)

Synthesis of Intermediate Compound 1e

[Chem. 12]

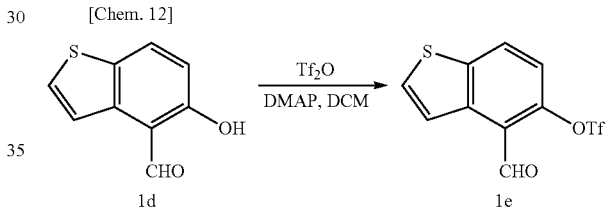

In the above scheme, Tf$_2$O represents trifluoromethanesulfonic anhydride, Tf represents trifluoromethylsulfonyl, and DMAP represents dimethylpropionamide.

Trifluoromethanesulfonic anhydride (52 mL, 30.9 mmol) was added to a dichloromethane (600 mL) solution of compound 1d (10.6 g, 59.5 mmol) and dimethylpropionamide (18.2 g, 149 mmol) under an argon atmosphere at −10° C., and the mixed liquid was stirred at room temperature (28° C.) for 30 minutes. The reaction was ceased by pouring 200 mL of water at 0° C. This was washed twice with 350 mL of 1 mol/L hydrochloric acid and twice with 300 mL of saturated brine, dried over sodium sulfate, and then concentrated under reduced pressure to give compound 1e as a fluorescent solid.

$^1$H-NMR (CDCl$_3$, RT) δ: 10.61 (s, 1H), 8.45 (d, 1H, J=5.4 Hz), 8.19 (d, 1H, J=8.4 Hz), 7.87 (d, 1H, J=5.4 Hz), 7.40 (d, 1H, J=8.4 Hz)

Synthesis of Intermediate Compound 1g

[Chem. 13]

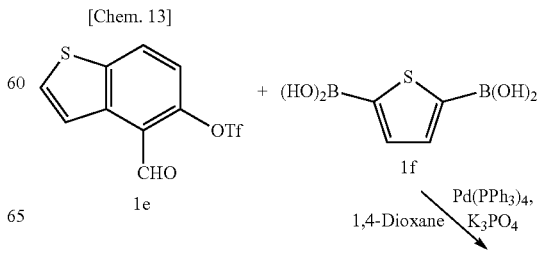

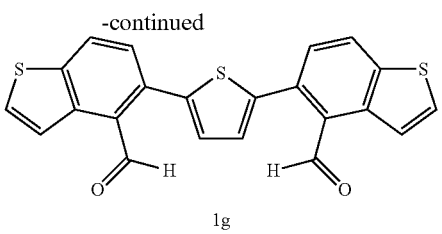

1g

Compound 1e (49.3 mmol), compound 1f (3.68 g, 21.4 mmol), and a mixed solvent of tripotassium phosphate (17.1 g, 64.3 mmol), 600 mL of 1,4-dioxane, and 60 mL of water were added to a 1 L three-necked flask, and the mixture was purged with argon three times, then tetrakis(triphenylphosphine)palladium (11.4 g, 9.86 mmol) was added thereto, and the mixed liquid was stirred at 110° C. for 12 hours. The mixed liquid was cooled to room temperature (28° C.), and then 200 mL of an aqueous ammonium chloride solution was poured. This was extracted with ethyl acetate, and concentrated under reduced pressure to give a yellow solid. This was washed with a mixed solvent (petroleum ether:ethyl acetate=10:1 (volume ratio)) and filtered to give compound 1g (15.3 g) as a yellow solid.

$^1$H-NMR (CDCl$_3$, RT) δ: 10.43 (s, 1H), 8.50 (d, 2H, J=5.4 Hz), 8.16 (d, 2H, J=8.2 Hz), 7.78 (d, 2H, J=5.4 Hz), 7.61 (d, 2H, J=8.2 Hz), 7.17 (s, 2H)

Synthesis of Intermediate Compound 1h

[Chem. 14]

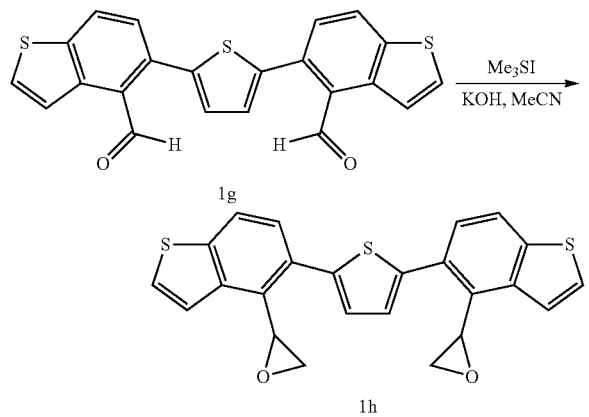

In the above scheme, MeCN represents acetonitrile.

A 2 L three-necked flask was charged with compound 1 g (31.1 mmol), potassium hydroxide (powder, 9.6 g, 171 mmol), and trimethyliodosulfur (19.1 g, 93.4 mmol), and the mixture was purged with argon for 30 minutes, and then 1600 mL of acrylonitrile was added. The suspension was stirred at from 65 to 70° C. for 12 hours. After cooling to room temperature (28° C.), unreacted potassium hydroxide was removed from the suspension by filtration, and 1000 mL of water was poured. This was extracted four times with 500 mL of dimethyl methane and concentrated under reduced pressure to give a brown solid. This was purified by column chromatography (developing solvent=petroleum ether:ethyl acetate=10:1 (volume ratio)) to give compound 1 h (8.1 g, 18.7 mmol, yield: 60%) as a brown solid.

$^1$H-NMR (CDCl$_3$, RT) δ: 7.87-7.90 (m, 4H), 7.55 (d, 1H, J=5.6 Hz), 7.49 (d, 1H, J=8.4 Hz), 7.15 (s, 2H), 4.45-4.46 (m, 1H), 3.15-3.17 (m, 1H), 2.83-2.86 (m, 1H)

Synthesis of Compound 1i

[Chem. 15]

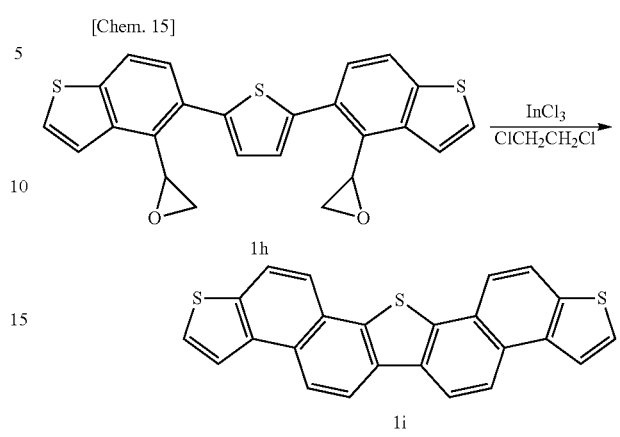

A 2 L three-necked flask was charged with indium trichloride (870 mg, 3.93 mmol), and heated under reduced pressure for 30 minutes using a hot gun. Compound 1 h (3.40 g, 7.86 mmol) was added to this, and the mixture was purged with argon three times, and then 1300 mL of dichloromethane was added. The suspension was stirred for 48 hours while refluxing. After cooling to room temperature (28° C.), and 500 mL of water was poured. This was extracted four times with 500 mL of dichloromethane and concentrated under reduced pressure to give a brown solid. This was washed three times with 300 mL of methanol, twice with 300 mL of water, and three times with 300 mL of methanol, and dried under reduced pressure to give grey solid 1i (3.05 g, 7.70 mmol, yield: 98%).

$^1$H-NMR (CDCl$_2$CDCl$_2$, 120° C.) δ: 8.39-8.50 (m, 4H), 8.08-8.22 (m, 6H), 7.68-7.73 (m, 2H)

Synthesis of Intermediate Compound 1j

[Chem. 16]

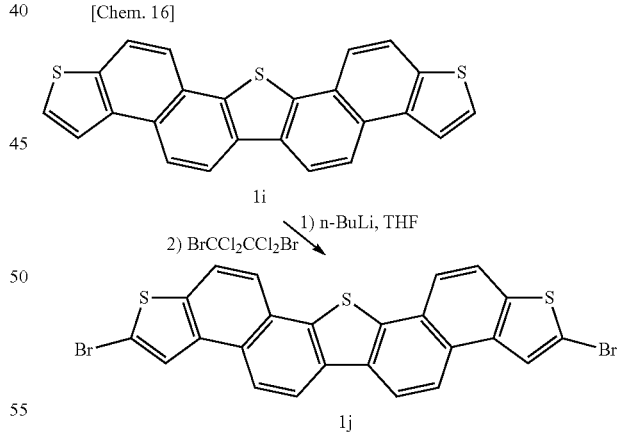

1) A 1 L three-necked flask was charged with compound 1i (4.56 g, 11.5 mmol) and dried under an argon atmosphere for 30 minutes, then 600 mL of tetrahydrofuran (water absorption: less than 50 ppm) was added thereto; the mixture was cooled to −60° C., then normal butyllithium (1.6 mol/L hexane solution, 25.1 mL, 40 mmol) was added, and the mixed liquid was stirred at −60° C. for 30 minutes. The mixed liquid was changed in color from brown to green, then heated to −10° C. and stirred for 30 minutes, then cooled again to −60° C. and stirred for 2 hours.

2) After confirming lithiation from ¹H-NMH, 1,2-dibromo-1,1,2,2-tetrachloroethane (13.0 g, 40 mmol) was added to the mixed liquid, and the resultant mixed liquid was stirred at −60° C. for 12 hours. After heating to room temperature (28° C.), 200 mL of water was poured. This was extracted with ethyl acetate and concentrated under reduced pressure to give a brown solid. This was washed three times with 300 mL of methanol, twice with 300 mL of water, twice with 300 mL of methanol, and once with 100 mL of dichloromethane, and then dried under reduced pressure to give compound 1j (6.04 g, 10.9 mmol, yield: 95%) as a grey solid.

¹H-NMR (CDCl$_2$CDCl$_2$, 120° C.) δ:7.9-8.5 (m, 10H)

Synthesis of Compound C10-TBNT

Production of Organic Thin Film Transistor

An organic semiconductor solution composition was prepared by mixing the compound C10-TBNT in the orthodichlorobenzene to attain 0.1 wt. % and heating the mixture at 120° C. for 3 hours.

A surface of a thermal oxide film of an n-type silicon substrate (20 mm×20 mm, thickness: 0.4 mm) having a thermal oxide film (silicon oxide film) having a thickness of 500 nm on a surface thereof was subjected to ultraviolet-ozone cleaning and treated with 0-phenethyltrimethoxysilane.

A glass member (10 mm×2 mm, thickness: 5 mm) was placed at the center of the β-phenethyltrimethoxysilane-treated surface of the substrate in close contact therewith,

[Chem. 17]

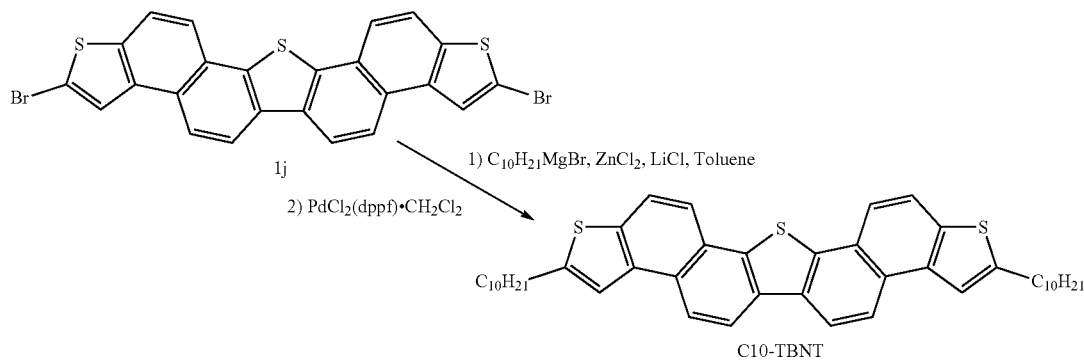

In the above scheme, PdCl$_2$(dppf).CH$_2$Cl$_2$ represents [1,1'-bis(diphenylphosphino)ferrocene] dichloropalladium·dichloromethane acetate.

1) Under an argon atmosphere, zinc chloride (1.0 mol/L tetrahydrofuran solution, 1.44 mL, 1.44 mmol) and lithium chloride (0.5 mol/L tetrahydrofuran solution, 2.88 mL, 1.44 mmol) were added to a toluene (23 mL) solution of normal decylmagnesium bromide (0.73 mol/L tetrahydrofuran solution, 1.85 mL, 1.35 mmol) at 0° C., and the mixture was stirred at 0° C. for 20 minutes to obtain a colorless and transparent zinc reagent solution.

2) Compound 1j (250 mg, 0.451 mmol) and a [1,1'-bis(diphenylphosphino)ferrocene] dichloropalladium·dichloromethane complex (29.5 mg, 0.0361 mmol) were added to the zinc reagent solution at room temperature (28° C.), and the mixture was heated to 100° C. with stirring and further stirred for 2 hours. After gradually cooling to room temperature (28° C.), a solid was precipitated by pouring methanol and filtered off and dried under reduced pressure to obtain a crude product. To the composition product, 140 mL of orthodichlorobenzene was added, and the mixture was heated to 120° C. to obtain a solution. The solution was purified by passing the solution through silica gel, and further purified (recrystallization solvent=orthodichlorobenzene, heated and dissolved at 80° C., then gradually cooled to 28° C.) by recrystallization to obtain compound C10-TBNT (218 g, 0.321 mmol, yield: 71%) as a cream-colored solid.

¹H-NMR (CDCl$_2$CDCl$_2$, 100° C.) δ:8.35 (d, 2H, J=8.7 Hz, ArH), 8.32 (d, 2H, J=8.7, Hz, Ar), 8.06 (d, 2H, J=8.7, Hz, ArH), 7.95 (d, 2H, J=8.7, Hz, Ar), 7.73 (s, 2H, ArH), 3.04 (t, 4H, J=7.3, Hz, Ar—CH$_2$), 1.82-1.89 (m, 4H, Ar—CH$_2$—CH$_2$), 1.29-1.57 (m, 28H, Ar—CH$_2$—CH$_2$—C$_7$—H$_{14}$), 0.88 (t, 6H, J=7.1 Hz, CH$_3$)

and the substrate was heated to 50° C. Then, using a pipette, one drop (about 0.05 mL) of the organic semiconductor solution composition was dropped from the side of the glass member to form a liquid film surrounding the glass member and having a concave meniscus.

The liquid film was heated and dried under atmospheric pressure at a substrate of 110° C. for 2 hours and further under reduced pressure (10-3 Pa) at 80° C. for 12 hours, and crystals of compound C10-TBNT was precipitated. Then, the glass member was removed, and thus a ring-shaped organic semiconductor film (film thickness: 50 nm) having a uniform thickness was formed on the substrate.

The organic semiconductor film was masked, and tetracyanoquinodimethane was vapor-deposited (thickness: 2 nm), and then gold was vapor-deposited (thickness: 40 nm) to obtain an organic thin film transistor for measuring field effect transistor properties (a gate width (W): 110 μm, a gate length (L): 100 μm, and a ratio (W/L): 1.1) for the source electrode and the drain electrode).

Evaluation of Carrier Mobility

The obtained organic thin film transistor was evaluated for the carrier mobility of compound C10-TBNT according to the method described above. As a result, the carrier mobility was 2.2 cm$^2$/Vs.

Example 2

The following compound C9-TBNT was synthesized from compound 1j obtained in the same manner as in Example 1, and the carrier mobility was evaluated in the same manner as in Example 1.

Synthesis of Compound C9-TBNT

[Chem.18]

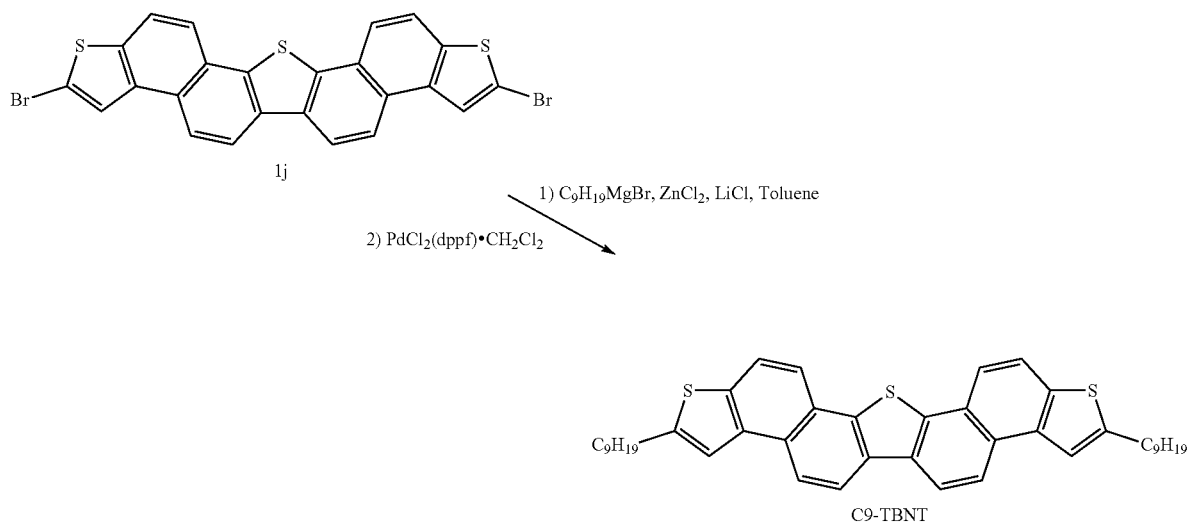

1) Under an argon atmosphere, zinc chloride (1.0 mol/L tetrahydrofuran solution, 1.73 mL, 1.73 mmol) and lithium chloride (0.5 mol/L tetrahydrofuran solution, 3.46 mL, 1.73 mmol) were added to a toluene (27 mL) solution of normal nonylmagnesium bromide (0.7 mol/L tetrahydrofuran solution, 2.29 mL, 1.62 mmol) at 0° C., and the mixture was stirred at 0° C. for 20 minutes to obtain a colorless and transparent zinc reagent solution.

2) Compound 1j (300 mg, 0.541 mmol) and a [1,1'-bis(diphenylphosphino)ferrocene]dichloropalladium·dichloromethane complex (35.4 mg, 0.0433 mmol) were added to the zinc reagent solution at room temperature (28° C.), and the mixture was heated to 100° C. with stirring and further stirred for 3 hours. After gradually cooling to room temperature (28° C.), a solid was precipitated by pouring methanol and filtered off and dried under reduced pressure to obtain a crude product. To the composition product, 360 mL of orthodichlorobenzene was added, and the mixture was heated to 120° C. to obtain a solution. The solution was purified by passing the solution through silica gel, and further purified (recrystallization solvent=orthodichlorobenzene, heated and dissolved at 80° C., then gradually cooled to 28° C.) by recrystallization to obtain compound C9-TBNT (256 g, 0.378 mmol, yield: 70%) as a cream-colored solid.

$^1$H-NMR (CDCl$_2$CDCl$_2$, 100° C.) δ:8.35 (d, 2H, J=8.7 Hz, ArH), 8.32 (d, 2H, J=8.7, Hz, ArH), 8.06 (d, 2H, J=8.7, Hz, ArH), 7.95 (d, 2H, J=8.7, Hz, ArH), 7.73 (s, 2H, ArH), 3.04 (t, 4H, J=7.6, Hz, Ar—CH$_2$), 1.82-1.89 (m, 4H, Ar—CH$_2$—CH$_2$), 1.30-1.56 (m, 24H, Ar—CH$_2$—CH$_2$—C$_6$H$_{12}$), 0.89 (t, 6H, J=6.4 Hz, CH$_3$)

For compound C9-TBNT, the carrier mobility was 6.6 cm$^2$/Vs.

Comparative Example 1

The following Comparative compound 1 was synthesized according to the synthesis method described in Patent Document 3 (WO 2013/125599), and the carrier mobility was evaluated in the same manner as in Example 1. The carrier mobility was 1.0 cm$^2$/Vs.

[Chem. 19]

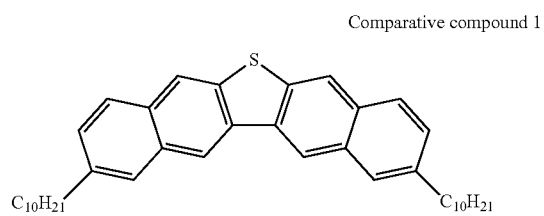

Comparative compound 1

From the above, it was found that the organic semiconductor materials of Examples 1 and 2 exhibited superior carrier mobility to that of the organic semiconductor material of Comparative Example 1.

INDUSTRIAL APPLICABILITY

By applying the organic semiconductor solution composition containing the compound according to the present invention to an ink-jet printing method or an edge casting method, high performance organic semiconductor films and organic thin film transistors can be obtained at low cost.

REFERENCE SIGNS LIST

10: Organic thin film transistor
100: Substrate
101: Conductive film (gate electrode)
102: Gate insulating film
103: Organic semiconductor film
104A: Conductive film (source electrode)
104B: Conductive film (drain electrode)
105: Protective layer

The invention claimed is:

1. A compound represented by Formula (1):

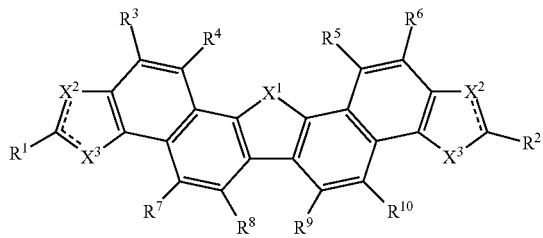

(1)

where in Formula (1), $X^1$ is an oxygen atom, a sulfur atom, a selenium atom, or a tellurium atom; $X^2$ and $X^3$, which may be the same or different, are each a carbon atom, an oxygen atom, a sulfur atom, a selenium atom or a tellurium atom, with the proviso that a case of $X^2$ and $X^3$ being simultaneously carbon atoms is excluded; $R^1$ and $R^2$, which may be the same or different, are each a hydrogen atom or an organic group, and $R^3$ to $R^{10}$, which may be the same or different, are each a hydrogen atom, a halogen atom, or an organic group; $R^3$ and $R^4$, $R^5$ and $R^6$, $R^7$ and $R^8$, $R^8$ and $R^9$, and $R^9$ and $R^{10}$ may each bond to each other to form a ring; and a double line including a dashed line represents a single bond or a double bond.

2. The compound according to claim 1, represented by Formula (1'):

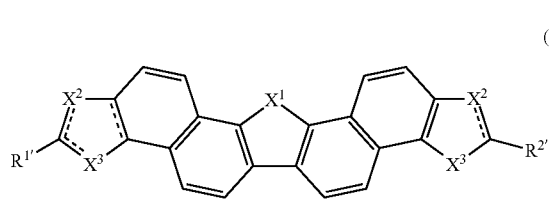

(1')

wherein in Formula (1'), $X^1$, $X^2$ and $X^3$ are the same as those in Formula (1); $R^{1'}$ and $R^{2'}$ are the same or different organic groups; and a double line including a dashed line represents a single bond or a double bond.

3. The compound according to claim 2, wherein, in Formula (1'), $X^1$ is a sulfur atom; one of $X^2$ and $X^3$ is a carbon atom and the other is a sulfur atom; and $R^{1'}$ and $R^{2'}$ are the same or different organic groups.

4. A method of manufacturing the compound described in claim 1, comprising obtaining a compound represented by Formula (1-5) from a compound represented by Formula (1-4):

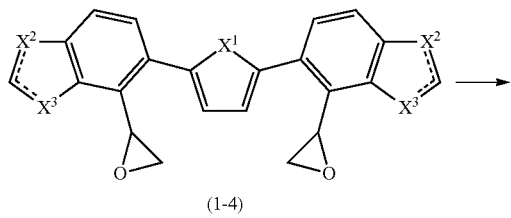

(1-4)

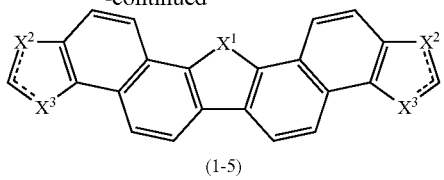

(1-5)

wherein in Formulas (1-4) and (1-5), $X^1$, $X^2$, $X^3$, and the double line including a dashed line indicate the same contents as those of Formula (1).

5. An organic semiconductor solution composition comprising the compound described in claim 1 and at least one solvent.

6. An organic semiconductor film formed from the organic semiconductor solution composition described in claim 5.

7. An organic thin film transistor comprising the organic semiconductor film described in claim 6.

8. The compound according to claim 1, wherein $X^1$ is a sulfur atom.

9. The compound according to claim 1, wherein $X^2$ is a sulfur atom and $X^3$ is a carbon atom.

10. The compound according to claim 1, wherein the organic groups according to $R^1$ and $R^2$ are alkyl groups having from 1 to 40 carbon atom(s).

11. The compound according to claim 1, wherein the organic groups in $R^1$ and $R^2$ are the same and linear or branched alkyl groups having from 1 to 20 carbon atom(s).

12. The compound according to claim 3, represented by Formula (1"):

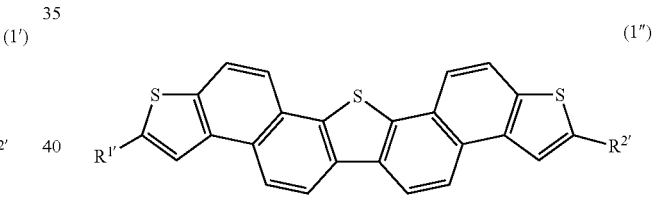

(1")

where in Formula (1"), $R^{1'}$ and $R^{2'}$ are the same or different organic groups; and a double line including a dashed line represents a single bond or a double bond.

13. The compound according to claim 12, wherein the organic groups in $R^{1'}$ and the $R^{2'}$ are alkyl groups having from 1 to 40 carbon atom(s).

14. The compound according to claim 12, wherein the organic groups in $R^{1'}$ and $R^{2'}$ are the same and linear or branched alkyl groups having from 1 to 20 carbon atom(s).

15. A method of manufacturing the compound described in claim 2, comprising obtaining a compound represented by Formula (1-5) from a compound represented by Formula (1-4):

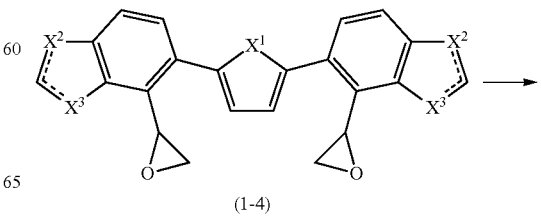

(1-4)

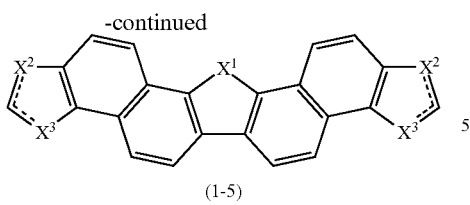

(1-5)

wherein in Formulas (1-4) and (1-5), $X^1$, $X^2$, $X^3$, and the double line including a dashed line indicate the same contents as those of Formula (1).

16. An organic semiconductor solution composition comprising the compound described in claim 12 and at least one solvent.

17. An organic semiconductor film formed from the organic semiconductor solution composition described in claim 16.

18. An organic thin film transistor comprising the organic semiconductor film described in claim 17.

* * * * *